(12) United States Patent
Harlin et al.

(10) Patent No.: US 10,100,259 B2
(45) Date of Patent: Oct. 16, 2018

(54) METHODS OF DEOXYGENATION OF TALL OIL AND PRODUCTION OF POLYMERIZABLE MONOMERS THEREFROM

(71) Applicant: STORA ENSO OYJ, Helsinki (FI)

(72) Inventors: Ali Harlin, Kerava (FI); Olli Aaltonen, Helsinki (FI); Antero Laitinen, Kirkkonummi (FI); Jari Räsänen, Imatra (FI); Outi Kylliäinen, Imatra (FI)

(73) Assignee: STORA ENSO OYJ, Helsinki (FI)

( * ) Notice: Subject to any disclaimer, the term of this patent is extended or adjusted under 35 U.S.C. 154(b) by 25 days.

(21) Appl. No.: 14/394,232

(22) PCT Filed: Apr. 12, 2013

(86) PCT No.: PCT/FI2013/050406
§ 371 (c)(1),
(2) Date: Oct. 13, 2014

(87) PCT Pub. No.: WO2013/153287
PCT Pub. Date: Oct. 17, 2013

(65) Prior Publication Data
US 2015/0175500 A1 Jun. 25, 2015

(30) Foreign Application Priority Data
Apr. 13, 2012 (FI) .................................. 20125407

(51) Int. Cl.
*C10G 3/00* (2006.01)
*C07C 1/24* (2006.01)
(Continued)

(52) U.S. Cl.
CPC ............. *C10G 3/50* (2013.01); *C07C 1/24* (2013.01); *C07C 4/04* (2013.01); *C10G 3/42* (2013.01);
(Continued)

(58) Field of Classification Search
CPC .................................. C10G 3/46; C10G 3/50
See application file for complete search history.

(56) References Cited

U.S. PATENT DOCUMENTS 2,863,914 A 12/1958 Raecke
2,891,992 A 6/1959 Raecke et al.
(Continued)

FOREIGN PATENT DOCUMENTS

DE 195 21 222 A1 12/1996
EP 1 194 236 B1 11/2003
(Continued)

OTHER PUBLICATIONS

European Search Report for European Patent Application No. 13775002.2, dated Nov. 6, 2015, 6 pages.
(Continued)

*Primary Examiner* — In Suk C Bullock
*Assistant Examiner* — Alyssa L Cepluch
(74) *Attorney, Agent, or Firm* — Patterson Thuente Pedersen, P.A.

(57) ABSTRACT

A method of deoxygenation of tall oil as well as methods for the production of aliphatic hydrocarbons and polymerizable monomers from tall oil. Sulphurous crude tall oil together with hydrogen gas is fed into a reactor comprising a catalyst bed. The oil is catalytically deoxygenated by hydrogen in the bed by use of a sulfided metal catalyst, e.g. a NiMoS catalyst. The flow exiting the reactor is cooled down and a hydrocarbon-bearing liquid phase is separated from a gas phase, followed by subjecting the liquid phase to distillation
(Continued)

for removal of useless aromatic hydrocarbons and then to steam cracking to form a product containing olefins such as ethylene or propylene. By regulation of the deoxygenation temperature to be at least 270° C. but less than 360° C. the yield is rich in linear and cyclic aliphates that usefully turn to olefins in the steam cracking, while formation of napthalenes is reduced.

10 Claims, 1 Drawing Sheet

(51) Int. Cl.
  *C07C 4/04* (2006.01)
  *C10G 9/36* (2006.01)
(52) U.S. Cl.
  CPC .................. *C10G 3/46* (2013.01); *C10G 9/36* (2013.01); *C07C 2527/043* (2013.01); *C10G 2300/1011* (2013.01); *C10G 2400/20* (2013.01); *Y02P 30/20* (2015.11)

(56) References Cited

U.S. PATENT DOCUMENTS

| | | | |
|---|---|---|---|
| 3,312,635 | A | 4/1967 | Liquori |
| 4,300,009 | A | 11/1981 | Haag et al. |
| 5,424,051 | A * | 6/1995 | Nagji ............... B01D 53/04 423/234 |
| 5,705,722 | A | 1/1998 | Monnier et al. |
| 8,957,269 | B2 | 2/2015 | Harlin et al. |
| 2004/0230085 | A1 | 11/2004 | Jakkula et al. |
| 2007/0131579 | A1 | 6/2007 | Koivusalmi et al. |
| 2007/0135669 | A1 | 6/2007 | Koivusalmi et al. |
| 2008/0154073 | A1 | 6/2008 | Petri et al. |
| 2008/0161620 | A1 | 7/2008 | Bozzano et al. |
| 2008/0308457 | A1 | 12/2008 | Dindi et al. |
| 2009/0300970 | A1 * | 12/2009 | Perego ............... C10G 3/47 44/307 |
| 2010/0292517 | A1 | 11/2010 | Debuisschert et al. |
| 2011/0049012 | A1 | 3/2011 | Stigsson et al. |
| 2011/0160505 | A1 * | 6/2011 | McCall ............... C07C 9/16 585/310 |
| 2011/0319683 | A1 | 12/2011 | Abhari et al. |
| 2013/0178650 | A1 | 7/2013 | Harlin et al. |

FOREIGN PATENT DOCUMENTS

| | | |
|---|---|---|
| EP | 2 003 159 A1 | 12/2008 |
| EP | 2 130 812 B1 | 8/2011 |
| FI | 121626 | 7/2010 |
| GB | 2 398 073 A1 | 8/2004 |
| WO | WO 99/10450 | 3/1999 |
| WO | WO 2007/133973 A2 | 11/2007 |
| WO | WO 2008/027699 A2 | 3/2008 |
| WO | WO 2008/067112 A2 | 6/2008 |
| WO | WO 2008/101945 A1 | 8/2008 |
| WO | WO 2009/004181 A2 | 1/2009 |
| WO | WO 2009/120457 A2 | 10/2009 |
| WO | WO 2010/028717 A2 | 3/2010 |
| WO | WO 2010/028717 A3 | 3/2010 |
| WO | WO 2010/086507 A1 | 8/2010 |
| WO | WO 2011/012439 A1 | 2/2011 |
| WO | WO 2011/053166 A1 | 5/2011 |
| WO | WO 2011/148045 A1 | 12/2011 |
| WO | WO 2011/151528 A1 | 12/2011 |

OTHER PUBLICATIONS

Jinto Manjaly Anthonykutty et al., "Upgrading of fatty acid containing rosin acids in to high value hydrocarbons via catalytic hydrodeoxygenation" 8th European Congress of Chemical Engineering, Sep. 25-29, 2011, Berlin, Germany, 23 pages.
Application and File History for U.S. Appl. No. 13/701,664, filed Feb. 18, 2013.
B. Holmbom "Composition of Tall Oil Pitch", Journal of the American Oil Chemists' Society, vol. 55, Mar. 1978, pp. 342-345.
Lars-Hugo Norlin et al., "Tall Oil", 2005 Wiley-VCH Verlag GmbH & Co., KGaA, Weinheim, pp. 1-14, Sandarne, Sweden.
C.E. Senseman et al., "Catalytic Oxidation of p-Cymene in the Vapor Phase", Bureau of Chemistry and Soils, U.S. Department of Agriculture, Washington, D.C., Industrial and Engineering Chemistry, Oct. 1931, pp. 1129-1131.
Internet: Wikipedia/Naphtha, hhttp://en.wikipedia.org/w/index.php?title=Naphth&oldid=363432035, julk, May 21, 2010, 5 pages.
Supplementary Partial European Search Report for EP Application 11789319.8, dated Jun. 17, 2014.
Opposition for Finnish Patent No. FI 125507 B, dated Jul. 18, 2016, 16 pages.

* cited by examiner

METHODS OF DEOXYGENATION OF TALL OIL AND PRODUCTION OF POLYMERIZABLE MONOMERS THEREFROM

PRIORITY CLAIM

This application is a National Phase entry of PCT Application No. PCT/FI2013/050406, filed Apr. 12, 2013, which claims priority to Finland Application No. 20125407, filed Apr. 13, 2012, the disclosures of which are hereby incorporated by reference herein in their entirety.

FIELD OF THE INVENTION

The present invention concerns a method of deoxygenation of tall oil and methods for the production of aliphatic hydrocarbons and polymerizable monomers, such as ethylene and propylene, from tall oil.

BACKGROUND OF THE INVENTION

Polymers have conventionally been produced from crude oil of fossil origin. In recent times biopolymers made from renewable raw materials have increasingly been studied as an alternative. One such raw material is tall oil obtained as a byproduct from cellulosic pulp cooking process.

Tall oil contains fatty acids and resin acids, which can be subjected to catalytic hydrodeoxygenation (HDO) and cracking, yielding a hydrocarbon-bearing liquid product as well as gas and water. The liquid hydrocarbons have been turned to biofuels, but there is even literature on turning them to monomeric compounds, which can serve as starting materials for the production of polymers.

WO 2011/151528 describes catalytic hydrodeoxygenation of various tall oil materials, such as crude tall oil (CDO), distilled tall oil (DTO) or tall oil fatty acids (TOFA), followed by separation of suitable aromatic hydrocarbons such as p-xylene or o-xylene from the liquid product and oxidizing them to terephthalic acid useful for the production of polyethylene terephthalate of biologic origin (bio-PET).

WO 2010/086507 teaches a process for the production of polymerizable ethylene and propylene from a distilled mixture of at least 75% of tall oil fatty acids and no more than 25% of tall oil resin acids, which is subjected to catalytic deoxygenation with hydrogen, followed by subjecting the yield of liquid hydrocarbons to steam cracking, which yields said monomers.

In order to produce bio-based olefinic monomers such as ethylene or propylene by a simpler process and with increased yield it would be desirable to use crude tall oil as the starting material, instead of acids purified by distillation. The reason for purifying the acids has been the tendency of the impurities to poison the catalyst. Even the resin acids present in crude tall oil have been regarded as less desirable, producing aromatic hydrocarbons that could not be turned to polymerizable olefins by hydrocracking.

SUMMARY OF THE INVENTION

The problem to be solved by the invention is to achieve an improved process allowing use of crude tall oil as starting material for catalytic hydrodeoxygenation as well as subsequent steam cracking for obtaining polymerizable olefins, without the need of distilling or otherwise purifying the tall oil, without deterioration of the catalyst, and with improved yield of aliphatic and non-aromatic cyclic hydrocarbons from the deoxygenating step as well as improved yield of olefinic monomers from the steam cracking step.

As a first aspect of the invention, the above problem is solved by a method of deoxygenation of crude tall oil comprising the steps of:
(i) feeding sulphurous crude tall oil and hydrogen gas into a catalyst bed, and
(ii) catalytically deoxygenating the oil in the bed with hydrogen in a temperature of at least 270° C. but below 360° C., by use of a sulfided metal catalyst.

According to a second aspect of the invention there is provided a method for the production of aliphatic hydrocarbons from tall oil, comprising the steps of:
(i) feeding sulphurous crude tall oil and hydrogen gas into a catalyst bed;
(ii) catalytically deoxygenating the oil by hydrogen in the bed in a temperature of at least 270° C. but below 360° C., by use of a sulfided metal catalyst;
(iii) recovering a hydrocarbon-bearing liquid from the yield of the deoxygenation; and
(iv) separating a fraction enriched with respect to aliphatic hydrocarbons by distillation.

According to a third aspect of the invention there is provided a method for the production of polymerizable olefinic monomers from tall oil, comprising the steps of:
(i) feeding sulphurous crude tall oil and hydrogen gas into a catalyst bed;
(ii) catalytically deoxygenating the oil by hydrogen in the bed in a temperature of at least 270° C. but below 360° C., by use of a sulfided metal catalyst;
(iii) cooling the flow which has exited the bed, and separating a hydrocarbon-bearing liquid phase from a gas phase; and
(iv) subjecting the hydrocarbon-bearing liquid to steam cracking to form a product containing polymerizable olefins.

An advantage gained by the invention is a reduced share of polyaromatic hydrocarbons in the yield of the deoxygenation stage. Working in temperatures below 360° C. has been found to be essential for achieving the improvement. Polyaromatics cannot be turned to polymerizable monomers by steam cracking and are therefore wasted in view of the production of biopolymers, which are the principal goal of the invention.

The sulphur in the catalyst is essential for effective hydrodeoxygenation of fatty and resin acids, but as it has tended to escape in the process the catalyst has lost its effect as a result. However, by use of sulphurous crude tall oil according to the invention there is sulphur available to supplant any lost sulphur and thus maintain the presence of sulfided catalyst in the process.

The sulphurous crude tall oil forming the starting material for the processes of the invention may have a content of 30 to 70 weight-% of fatty acids and a content of 20 to 50 weight-% of resin acids. The content of sulphur in the sulphurous crude tall oil, stemming from the use of sulfuric acid to liberate the fatty and resin acids from black liquor tall oil soap, may be in the range of 0.05 to 0.5 weight-%.

The deoxygenation catalyst may be a sulfided NiMo or CoMo catalyst, preferably a catalyst comprising NiMoS. Such sulfided catalyst may be obtained by sulfiding the corresponding metal catalyst (NiMo, CoMo) by use of $H_2S$ and $H_2$.

According to a preferred embodiment of the invention the deoxygenation temperature is in the range of 280 to 350° C., preferably 280 to 320° C.

According to another embodiment of the invention the hydrogen pressure at the deoxygenation step is 30 to 100 bar.

According to a further embodiment of the invention the catalyst bed is a fixed bed formed by fixed bed material. The flows in the catalyst bed preferably run from top to bottom.

The gas phase that is separated from the hydrocarbon-bearing liquid phase after the deoxygenation stage may advantageously be treated with diethyl amine to separate the gaseous $C_1$-$C_4$-hydrocarbons contained therein. These hydrocarbons may usefully be passed to steam cracking, while the residue, rich in hydrogen gas, is circulated back to be used as hydrogen-bearing feed gas for the deoxygenation stage.

Beside the organic hydrocarbon-bearing liquid phase water is formed at the deoxygenation step, and preferably this aqueous phase is separated from the hydrocarbon-bearing liquid before feeding the latter into steam cracking.

Beside aliphatic and cyclic hydrocarbons the hydrocarbon-bearing liquid obtained from the deoxygenation step contains hydrocarbons that are in the boiling range of naphtha. Preferably any aromatic hydrocarbons are removed from the hydrocarbon-bearing liquid phase before the steam cracking step.

The preferred products made by steam cracking the hydrocarbon-bearing liquid are ethylene and propylene, useful for the production of polyethylene and polypropylene, respectively.

DETAILED DESCRIPTION OF THE INVENTION

Figure 1:
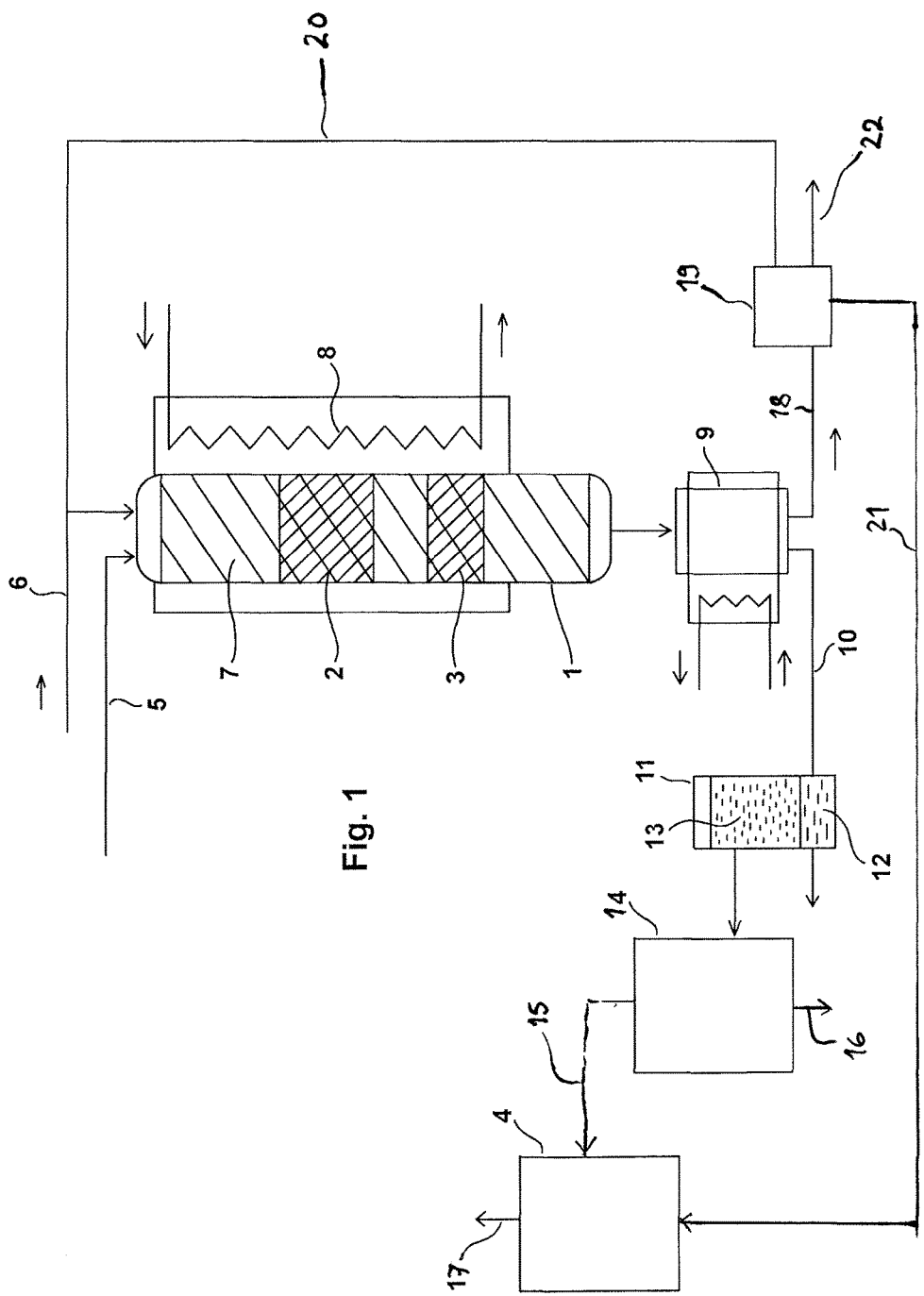
FIG. 1 is a schematic of an apparatus according to certain aspects of the present invention.

At first, the present invention is described with reference to the appended drawing (FIG. 1), which shows schematically an apparatus intended for the application of the invention.

According to FIG. 1, the process generally comprises treatment of sulphurous crude tall oil 5 in a vertical reactor 1 having catalytic deoxygenating and cracking zones 2, 3 in said order. The output from the reactor 1 is separated into fractions, and the obtained linear and cyclic aliphates in particular are further cracked in a steam cracking apparatus 4, as such known from the field of petrochemistry and operated in a manner known to a skilled person. The products of the steam cracking are olefins, such as ethylene or propylene, which are useful as monomers for the production of biopolymers.

The feed 5 of the crude tall oil, containing 30-70 weight-% of fatty acids and 20-50 weight-% of resin acids, as well as about 5 weight-% of sterols and/or stanols, 0.05-0.5 weight-% of sulphur etc. as minor components, is brought to an upper end of the reactor 1. In addition, hydrogen is fed to the upper end of the reactor 1 through a line 6. The reactor 1 is filled with quartz wool, which works as bed material 7 and the superimposed, separate zones 2, 3 of which comprise a NiMoS catalyst to deoxygenate the acids that were fed and a zeolite catalyst to crack carbon chains. The flow direction of the liquid and gas phases in the reactor 1 is from top to bottom. To adjust the reaction temperatures, the reactor 1 is provided with an electric heater 8.

The hot reaction products exiting through the lower end of the reactor 1 are conducted to a cooler 9, and the liquefied product moves through a line 10 to a separating tank 11, which separates the aqueous phase 12 from the oil phase 13. The oil phase 13 proceeds to a distillator 14, which separates saturated aliphatic as well as cyclic hydrocarbons as distillate 15 from a residue 16 of aromatic hydrocarbons and esters, which is discarded from the process. The residue 16 would not produce useful monomers in steam cracking, and removing the aromatics by distillation prevents them from fouling and eventually clogging the steam cracker 4. The distillate 15 then proceeds to steam cracking 4, wherein cracking into low-molecular olefins 17 as the desired end product takes place through several intermediary stages. The olefins are used as starting materials of the production of biopolymers, such as polyethylene or polypropylene.

The gases 18, which are not condensed in the cooler 9 and which contain hydrogen, oxides of carbon, possibly low-molecular hydrocarbons and other impurities, moves to a washer 19, treating the gas flow with diethyl amine. Pure hydrogen 20 is circulated back to the upper end of the reactor 1 to constitute part of the deoxygenating gas, a flow 21 of lower alkanes and water vapour are conducted to the steam cracker 4, and the oxides of carbon and other gaseous impurities 22 are removed from the process.

In a simpler implementation of the process according to the invention the zeolite catalyst 3 in the reactor 1 and, along with that, the catalytic cracking may be omitted. In that case, circulating 20 the hydrogen can also be omitted due to the minor amount or lack of hydrogen exiting the reactor. In other respects, the apparatus and the process flow are as illustrated in the drawing.

EXAMPLE

A series of eleven tests (1-11) was carried out by use of a sample of crude tall oil (CTO). Tests 1-5 were comparative and tests 6-11 accorded with the invention.

The sulphurous CTO stemmed from sulphate cooking process. Water was not added to the CTO before it was fed to deoxygenation. The reactor corresponded to the one described in FIG. 1. Hydrogen was used as the deoxygenating gas. The deoxygenation catalyst was NiMo presulfided with $H_2S$ and $H_2$ at 320° C. or a temperature gradually rising from 20 to 400° C. The deoxygenation temperature in the tests was in the range of 300-406° C., and the gas pressure was in the range of 50-56 bar. The liquid and gas products obtained from the catalytic deoxygenation were analysed. The results are shown in Table 1.

The most important finding from the results is that the share of aromatic hydrocarbons in the liquid product of deoxygenation is significantly reduced as the deoxygenation temperature was dropped from around 400° C. to 300-350° C. The change was accompanied by a rise in the share of useful paraffinic (aliphatic) and naphthenic (cyclic) hydrocarbons. As the yield is turned to polymerizable olefins by steam cracking, the final yield of olefins will be increased accordingly.

TABLE 1

| Sample | | 1 | 2 | 3 | 4 | 5 | 6 | 7 | 8 | 9 | 10 | 11 |
|---|---|---|---|---|---|---|---|---|---|---|---|---|
| Feedstock | | | | | | | | | | | | |
| CTO | g/h | 6.1 | 5.8 | 6.2 | 5.7 | 6.0 | 6.0 | 6.0 | 6.0 | 6.0 | 6.0 | 6.0 |
| Catalyst | | | | | | | | | | | | |
| NiMo | g | 3 | 3 | 3 | 3.1 | 3.1 | 6 | 6 | 6 | 8 | 8 | 8 |
| Presulfiding | | H2S + H2 320 C. | | | CTO 20-400 C. | | H2S + H2 320 C. | | | H2S + H2 320 C. | | |
| Reaction | | | | | | | | | | | | |
| Time on stream | h | 2-4 | 4-6 | 6-8 | 4-6 | 6-8 | 2-4 | 4-6 | 6-8 | 2-4 | 4-6 | 6-8 |
| Temperature | C. | 406 | 402 | 402 | 400 | 401 | 350 | 350 | 350 | 300 | 300 | 300 |
| Pressure | bar | 52 | 54 | 54 | 56 | 55 | 50 | 50 | 50 | 50 | 50 | 50 |
| WHSV based on HDO-catalyst & CTO | 1/h | 2 | 1.9 | 2 | 1.9 | 1.9 | 1.4 | 0.9 | 1.2 | 0.75 | 0.75 | 0.75 |
| Hydrogen feed | g/h | 0.67 | 0.67 | 0.67 | 0.67 | 0.67 | 0.73 | 0.73 | 0.73 | 0.73 | 0.73 | 0.73 |
| Hydrogen/CTO feed | w/w | 0.11 | 0.12 | 0.11 | 0.12 | 0.11 | 0.08 | 0.17 | 0.06 | 0.11 | 0.116 | 0.128 |
| Liquid product | | | | | | | | | | | | |
| Approximate yield, % from liquid feed | | 99 | 93 | 81 | 102 | 91 | 90 | 101 | 83 | 99 | 93 | 96 |
| Aqueous phase, % of total liquid product | | 7 | 11 | 12 | 7 | 7 | 10 | 12 | 14 | 4 | 13 | 16 |
| Composition, wt-% of GC-analyzed | | | | | | | | | | | | |
| Paraffinic | | 37.6 | 50.5 | 42.3 | 38.5 | 35.8 | 53.6 | 49.3 | 55.1 | 59.2 | 59.9 | 58.3 |
| Iso-paraffinic | | 11.6 | 5.4 | 7.8 | 12.9 | 11.6 | 5.4 | 5.1 | 5.1 | 2.5 | 2.8 | 1.9 |
| Olefins | | 0.0 | 0.0 | 0.0 | 0.0 | 0.0 | 0.0 | 0.0 | 0.0 | 0.0 | 0.0 | 0.0 |
| Naphtenic (cyclic) | | 20.9 | 19.2 | 22.0 | 25.3 | 26.6 | 25.1 | 23.3 | 21.6 | 22.6 | 20.3 | 21.0 |
| Monoaromatics | | 5.6 | 3.5 | 4.8 | 3.3 | 3.5 | 1.6 | 1.6 | 1.4 | 0.9 | 0.3 | 0.3 |
| Polyaromatics | | 18.1 | 12.0 | 20.2 | 13.7 | 14.3 | 7.7 | 9.6 | 6.2 | 5.1 | 7.0 | 7.0 |
| Esters | | 6.4 | 9.2 | 7.7 | 6.3 | 8.2 | 6.6 | 11.0 | 10.5 | 9.7 | 9.7 | 9.7 |
| Gas product | | | | | | | | | | | | |
| Approximate yield, % of liquid feed | | 8.8 | 9.1 | 8.6 | 7.6 | 7.3 | 7.7 | 9.4 | 6.9 | 5.3 | 6.5 | 6.5 |
| Composition, % of gaseous products: | | | | | | | | | | | | |
| | | average over 8 hours | | | average over 8 hours | | | | | | | |
| CO | | 15 | | | 18 | | 13.9 | 12.1 | 15.0 | 11.5 | 12.6 | 13.4 |
| CO2 | | 41 | | | 42 | | 62.4 | 52.4 | 62.1 | 67.7 | 68.5 | 68.7 |
| C1 + C2 | | 1 | | | 17 | | 11.1 | 15.5 | 10.5 | 15.5 | 14.0 | 14.3 |
| C3 | | 29 | | | 23 | | 12.6 | 19.7 | 12.1 | 4.9 | 4.4 | 3.4 |

The invention claimed is:

1. A method for the production of polymerizable olefins from tall oil, the method comprising the steps of:
feeding sulphurous crude tall oil and hydrogen gas into a catalyst bed, the sulphurous crude tall oil having a content of 30 to 70 weight-% of fatty acids and a content of 20 to 50 weight-% of resin acids;
catalytically deoxygenating the sulphurous crude tall oil by hydrogen in the catalyst bed in a temperature of 280° C. to 320° C. in the presence of a sulfided metal catalyst;
cooling the flow which has exited the catalyst bed, and separating a hydrocarbon bearing-liquid phase from a gas phase;
removing aromatic hydrocarbons from the hydrocarbon-bearing liquid phase to produce a hydrocarbon-bearing liquid distillate; and
subjecting the hydrocarbon-bearing liquid distillate to steam cracking to form a product containing polymerizable olefins.

2. The method of claim 1, wherein water is separated from the hydrocarbon-bearing liquid phase before feeding the liquid into steam cracking.

3. The method of claim 1, wherein the aromatic hydrocarbons are removed from the hydrocarbon-bearing liquid phase before the steam cracking step by distilling the hydrocarbon-bearing liquid phase to separate the aromatic hydrocarbons from the hydrocarbon-bearing distillate.

4. The method of claim 1 wherein ethylene and/or propylene are produced by the steam cracking.

5. The method of claim 1, wherein the gas phase comprises contaminants, hydrogen gas, and $C_1$ to $C_4$ hydrocarbons, and wherein the gas phase is washed with diethyl amine to remove the contaminants, the hydrogen gas is circulated to the deoxygenation stage to be used as hydrogen-bearing gas, and the $C_1$ to $C_4$ hydrocarbons are recovered and passed to steam cracking.

6. The method of claim 1, wherein the sulphurous crude tall oil contains 0.05 to 0.5 weight-% of sulphur.

7. The method of claim 1, wherein the deoxygenation catalyst is a sulfided NiMo or CoMo catalyst.

8. The method of claim 1, wherein the hydrogen pressure at the deoxygenation step is 30 to 100 bar.

9. The method of claim 1, wherein the catalyst bed is a fixed bed formed by fixed bed material.

10. The method of claim 1, wherein the flows in the catalyst bed run from top to bottom.

\* \* \* \* \*

UNITED STATES PATENT AND TRADEMARK OFFICE
CERTIFICATE OF CORRECTION

Page 1 of 1

PATENT NO. : 10,100,259 B2
APPLICATION NO. : 14/394232
DATED : October 16, 2018
INVENTOR(S) : Harlin et al.

It is certified that error appears in the above-identified patent and that said Letters Patent is hereby corrected as shown below:

On the Title Page

The first or sole Notice should read --

Subject to any disclaimer, the term of this patent is extended or adjusted under 35 U.S.C. 154(b) by 57 days.

Signed and Sealed this
Thirtieth Day of July, 2019

Andrei Iancu
*Director of the United States Patent and Trademark Office*